United States Patent [19]

Tsuto et al.

[11] 4,072,470

[45] Feb. 7, 1978

[54] GAS FEEDER FOR SULFONATION APPARATUS

[75] Inventors: Keiichi Tsuto, Wakayama; Kanji Majima, Chiba; Toshio Hirasaka, Yokohama, all of Japan

[73] Assignee: Kao Soap Co., Ltd., Tokyo, Japan

[21] Appl. No.: 780,820

[22] Filed: Mar. 23, 1977

[30] Foreign Application Priority Data

Mar. 31, 1976 Japan .............................. 51-39425[U]

[51] Int. Cl.[2] .................. C07C 143/02.16; B05B 7/06; B01J 4/00
[52] U.S. Cl. ...................................... 23/284; 23/285; 23/260; 23/283; 260/513 T; 239/428; 239/427.5; 239/431; 261/115; 261/116
[58] Field of Search ................. 23/284, 285, 260, 283; 261/115, 116; 260/513 T; 239/428, 427.5, 431

[56] References Cited

U.S. PATENT DOCUMENTS

| | | | |
|---|---|---|---|
| 2,923,728 | 2/1960 | Falk et al. | 260/513 T X |
| 3,277,145 | 10/1966 | Shull et al. | 23/284 X |
| 3,501,276 | 3/1970 | Vander Mey | 23/284 |
| 3,502,441 | 3/1970 | Hudson | 23/259.1 |
| 3,535,339 | 10/1970 | Beyer et al. | 260/513 T X |
| 3,918,917 | 11/1975 | Ashina et al. | 260/513 X |
| 3,931,273 | 1/1976 | Lanteri | 23/284 X |

*Primary Examiner*—James H. Tayman, Jr.
*Attorney, Agent, or Firm*—Blanchard, Flynn, Thiel, Boutell & Tanis

[57] ABSTRACT

A sulfonation apparatus comprising a gas feeder for feeding a first stream of $SO_3$-containing gas and a second stream of inert gas into contact with an annular film of sulfonatable material.

7 Claims, 3 Drawing Figures

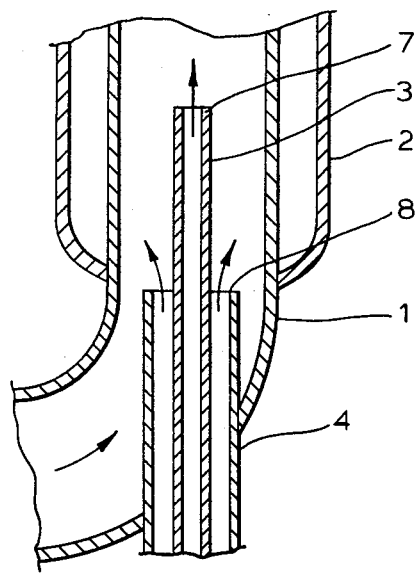
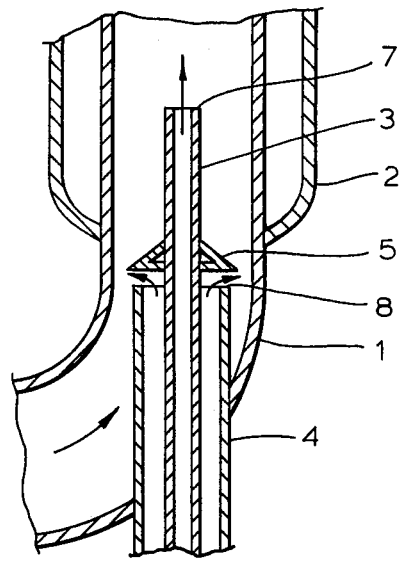
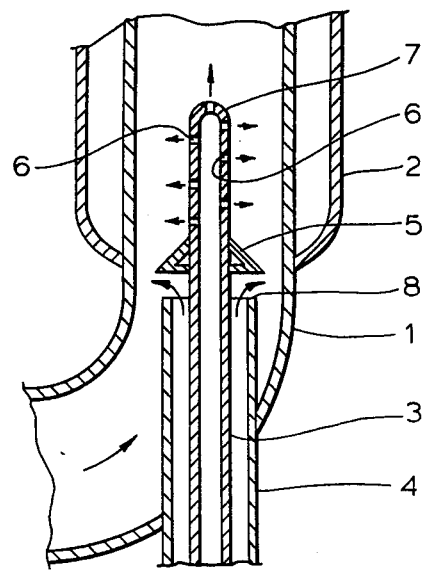

GAS FEEDER FOR SULFONATION APPARATUS

BACKGROUND OF THE INVENTION

1. Field of the Invention

This invention relates to an improved gas feeder for a sulfonation apparatus.

2. Description of the Prior Art

A preferred sulfonation process comprises flowing a gas containing $SO_3$ into a reaction tube and simultaneously flowing a liquid sulfonatable organic compound along the inner wall of the reaction tube in the form of a film whereby to effect gas-liquid contact between the $SO_3$ and the sulfonatable compound. Examples of such sulfonation process are disclosed in Japanese Patent Publication No. 37407/52, Japanese Patent Publication No. 8087/73 and Japanese Patent Application Laid-Open Specification No. 72123/73. These known methods, however, involve the disadvantage that if the gas containing $SO_3$ is not supplied under proper conditions, the organic compound adheres to the gas feed nozzle or injector and the resulting sulfonated product is colored by excessive contact with the $SO_3$, thereby reducing the quality of the sulfonated product. Especially in case of the multistage reaction, wherein the $SO_3$-containing gas is supplied at two or more stages, as disclosed in Japanese Patent Application Laid-Open Specification No. 72123/73, the risk of coloration of the sulfonated product owing to excessive reaction in the second and subsequent gas feed portions increases.

SUMMARY OF THE INVENTION

This invention overcomes the above disadvantage of the conventional sulfonation process. More specifically, in accordance with the present invention, there is provided a gas feeder for a sulfonation apparatus in which a liquid sulfonatable organic compound is flowed along the inner wall of a reaction tube in the form of a thin film and a gas containing $SO_3$ is flowed into the reaction tube for reactive contact with the sulfonatable compound, said gas feeder comprising a pair of coaxial gas feed tubes concentrically disposed in the reaction tube, with the upper end of the inner tube projecting above the upper end of the outer tube. The gas containing $SO_3$ is flowed in through the inner tube and an inert gas is flowed through the annular zone between the inner tube and the outer tube.

Preferred embodiments of the invention will now be described by reference to the accompanying drawings.

BRIEF DESCRIPTION OF THE DRAWINGS

FIG. 1 is a central cross-sectional view of one embodiment of the invention.

FIG. 2 is a central cross-sectional view of a second embodiment of the invention.

FIG. 3 is a central cross-sectional view of a third embodiment of the invention.

Referring to FIG. 1, a double-tube assembly consisting of an inner tube 3 and a coaxial outer tube 4 is concentrically disposed in the lower end of a sulfonation reaction tube 1. The reaction tube 1 and the double-tube assembly are concentric with one another at least in the zone in which the gas and the liquid contact each other. Accordingly, it is preferred that, as shown in FIG. 1, the tubes 3 and 4 are linear and are concentric with each other, the lower portion of the reaction tube 1 is curved and the upper portion of said reaction tube is concentric with the tubes 3 and 4. Of course, an arrangement reverse to the above-described arrangement may be adopted, that is, the reaction tube 1 can be linear and the lower portions of the tubes 3 and 4 can be curved. It is essential, however, that the tubes 1, 3 and 4 be coaxial and concentrically disposed in the zone where the gases supplied through tubes 3 and 4 contact the sulfonatable liquid supplied through tube 1. It is necessary that the upper end 7 of the inner tube 3 projects upwardly beyond the upper end 8 of the outer tube 4 a sufficient distance. If this projection distance is insufficiently long, the sulfonatable organic compound which rises in the form of an annular film on the inner wall of the reaction tube 1 from the lower portion thereof and also on the outer wall of the outer tube 4 can become present on and adhere to the upper end of the inner tube 3, resulting in coloration of the reaction product owing to excessive gas-liquid contact thereat. The distance that the upper end of tube 3 must project above the upper end of tube 4 to avoid excessive coloration of the reaction product can be determined by experimentation for any given installation based on the sizes of the tubes, the flow rates of the gases and the sulfonatable material, the viscosity of the sulfonatable material and similar considerations.

The distance H between the upper end of tubes 4 and 3 may be determined to be within the range between C and 5C, preferably 2C and 4C, in which C is a clearance between the tubes 4 and 3, as calculated by substracting the outer radius of the tube 3 from the inner radius of the tube 4. In the embodiment as in FIG. 1, H is 4C and in the embodiment as in FIG. 2, H is 2C.

In FIG. 1, reference numeral 2 indicates an external cooling jacket on the reaction tube 1 which is arranged to remove the reaction heat of the sulfonation reaction.

The risk of coloration can be eliminated in the present apparatus by positioning the upper end of the inner tube 3 upwardly beyond the upper end of the outer tube 4 as illustrated above. The upper end of the outer tube 4 is normally located close to the lower end of the cooling jacket 2. The upper end of the inner tube is located within the zone of the reaction tube 1 which is encircled by the cooling jacket.

Another preferred embodiment of the present invention will now be described by reference to FIG. 2.

In the embodiment shown in FIG. 2, a disc-like or frusto-conical baffle plate 5 having an outer diameter substantially equal to that of the outer tube 4 is sleeved on the outer surface of the projecting portion of the inner tube 3. The lower surface of plate 5 is located at a point close to and vertically spaced upwardly a short distance from the upper end 8 of the outer tube 4 and extends transversely to said outer tube. This baffle plate 5 exhibits the effect that if the organic compound adheres to and rises along the outer wall of the outer tube 4, the organic compound is deflected outwardly by the combined effects of the inert gas and the baffle plate and is prevented from rising in contact with the inner tube 3. Thus, the inert gas coming from the annular zone between the inner tube and the outer tube and impinging against the baffle plate 5 diverts any organic compound rising on the outer wall of the outer tube 4 toward the inner wall of the reaction tube 1 below the baffle plate.

Another preferred embodiment of the present invention will now be described by reference to FIG. 3.

In this embodiment, the top end 7 of the inner tube 3 is closed by an end wall. Circumferentially and vertically spaced openings 6 are provided in the portion of the inner tube that projects above the upper end of the outer tube 4 and is located above the baffle plate 5, as shown in FIG. 3. These openings direct the SO$_3$-containing gas in radial directions toward the inner wall of the reaction tube 1. As shown, there can be an opening 6 in the upper end wall of the inner tube for directing a portion of the SO$_3$-containing gas axially in the reaction tube 1. By this arrangement, SO$_3$ gas is uniformly blown toward the inner wall of the reaction tube 1, and in the structure shown in FIG. 3, even if some of the organic compound adheres to the upper end of the inner tube 3, it flows down on the outer wall of the inner tube and is blown away toward the inner wall of the reaction tube 1 below the baffle plate 5 by the inert gas. In contrast, in the embodiment shown in FIG. 1, the organic compound sometimes may adhere to the upper end 7 of the inner tube 3. Although this adhesion hardly takes place because of the upward extension of the upper end of the inner tube beyond the upper end of the outer tube, such adhesion may occur owing to interruption of the sulfonation operation or the like. Such adhering organic compound is blown up on both the inner and outer sides of the inner tube by the gases. Thus, there is a risk that the adhering organic compound will become stagnant and become colored due to excessively long contact with SO$_3$. In short, although the structure shown in FIG. 1 is improved in comparison with the conventional devices, the structure shown in FIG. 2 is an improvement on the structure shown in FIG. 1 and the structure shown in FIG. 3 is a further improvement on the structure shown in FIG. 2.

The embodiments of the invention in which an exclusive property or privilege is claimed are defined as follows:

1. In a sulfonation apparatus in which a sulfonatable organic compound is flowed along the inner wall of a reaction tube in the form of a film and a gas containing SO$_3$ is flowed in the reaction tube in concurrent flow relationship with the organic compound for gas-liquid reactive contact therewith, the improvement which comprises: apparatus for feeding said gas comprising a pair of concentric gas-feeding tubes disposed concentrically in said reaction tube whereby a gas containing SO$_3$ can be flowed in the inner gas-feeding tube and an inert gas can be flowed in the annular clearance between the inner gas-feeding tube and the outer gas-feeding tube, the upper portion of the inner gas-feeding tube projecting above the upper end of the outer gas-feeding tube so that the upper end of the inner gas-feeding tube is disposed a preselected distance above the upper end of the outer gas-feeding tube, a baffle plate mounted on the upper projecting portion of the inner gas-feeding tube at a location close to, but spaced upwardly from, the upper end of the outer gas-feeding tube so that the inert gas is deflected outwardly to impinge against the inner wall of the reaction tube so that the sulfonatable organic compound does not become colored excessively by contact with SO$_3$-containing gas that flows through said inner gas-feeding tube.

2. An apparatus as set forth in claim 1 wherein the baffle plate has a disc-like form.

3. An apparatus as set forth in claim 1 wherein the upper end of the inner gas-feeding tube is closed by an end wall and opening means are formed on the periphery of the upper projecting portion of the inner gas-feeding tube so that the SO$_3$-containing gas is directed to impinge against the inner wall of the reaction tube.

4. A sulfonation apparatus comprising an upright elongated reaction tube of circular cross-section, an external heat exchange jacket encircling said reaction tube, means for feeding a stream of liquid sulfonatable organic material into the lower end of said reaction tube to form an annular upwardly rising film of said material on the inner wall of said reaction tube, a pair of coaxial, inner and outer gas feeding tubes extending upwardly into the lower end of said reaction tube and concentric therewith, the inner gas-feeding tube extending above the upper end of the outer gas-feeding tube and being adapted for supplying a stream of SO$_3$-containing gas into said reaction tube, the outer gas-feeding tube terminating at a vertical location close to the lower end of said heat exchange jacket and being adapted to supply a stream of inert gas, both of said inner and outer gas-feeding tubes being open at their upper ends, an annular baffle plate mounted on said inner gas-feeding tube and positioned vertically upwardly spaced from, but close to, the upper end of said outer gas-feeding tube, said baffle plate having a lower surface of substantially the same size as said outer gas-feeding tube for directing the stream of inert gas outwardly toward said annular upwardly-rising film of said liquid sulfonatable organic material, said stream of SO$_3$-containing gas being directed upwardly in said reaction tube substantially coaxial with said film whereby said upwardly rising film of said sulfonatable organic material is contacted first by said stream of inert gas and then by said stream of SO$_3$-containing gas.

5. A sulfonation apparatus as claimed in claim 4 in which said baffle plate has an outwardly and downwardly inclined upper surface extending from the periphery of said inner tube.

6. A sulfonation apparatus comprising an upright elongated reaction tube of circular cross-section, an external heat exchange jacket encircling said reaction tube, means for feeding a stream of liquid sulfonatable organic material into the lower end of said reaction tube to form an annular upwardly rising film of said material on the inner wall of said reaction tube, a pair of coaxial, inner and outer gas-feeding tubes extending upwardly into the lower end of said reaction tube and concentric therewith, the inner gas-feeding tube extending above the upper end of the outer gas-feeding tube and being adapted for supplying a stream of SO$_3$-containing gas into said reaction tube, the outer gas-feeding tube terminating at a vertical location close to the lower end of said heat exchange jacket and being adapted to supply a stream of inert gas, said outer gas-feeding tube being open at its upper end, an annular baffle plate mounted on said inner gas-feeding tube and positioned vertically upwardly spaced from, but close to, the upper end of said outer gas-feeding tube, said baffle plate having a lower surface of substantially the same size as said outer gas-feeding tube for directing the stream of insert gas radially outwardly toward said annular upwardly-rising film of said liquid sulfonatable organic material, said inner gas-feeding tube being closed at its upper end and having a plurality of openings therethrough above said baffle plate for directing SO$_3$-containing gas into said reaction tube and against said film whereby said upwardly rising film of said sulfonatable organic material is contacted first by said stream of inert gas and then by said stream of SO$_3$-containing gas.

7. A sulfonation apparatus as claimed in claim 6 in which said baffle plate has an outwardly and downwardly inclined upper surface extending from the periphery of said inner tube.

* * * * *